United States Patent [19]

McKibben et al.

[11] 4,356,817
[45] Nov. 2, 1982

[54] INSERTER FOR VAGINAL PRODUCT

[75] Inventors: Gary E. McKibben, Cincinnati; Mary Jo Helseth, West Chester, both of Ohio

[73] Assignee: The Procter & Gamble Company, Cincinnati, Ohio

[21] Appl. No.: 165,540

[22] Filed: Jul. 3, 1980

[51] Int. Cl.³ .............................................. A61F 5/46
[52] U.S. Cl. ..................................... 128/127; 128/130
[58] Field of Search ................. 128/127, 130, 131, 263

[56] References Cited

U.S. PATENT DOCUMENTS

| 2,540,325 | 2/1951 | DeBray et al. | 128/127 |
| 2,818,856 | 1/1958 | Kohl | 128/127 |
| 2,830,582 | 4/1958 | Ljung | 128/127 |
| 3,103,929 | 9/1963 | Brecht | 128/263 |
| 3,965,891 | 6/1976 | Lerner | 128/130 |
| 4,191,517 | 5/1980 | Byrd et al. | 425/286 |

FOREIGN PATENT DOCUMENTS 1271008 7/1961 France .

Primary Examiner—Michael H. Thaler
Assistant Examiner—C. W. Shedd
Attorney, Agent, or Firm—E. Kelly Linman; John V. Gorman; Richard C. Witte

[57] ABSTRACT

An apparatus for safely and reliably inserting a generally hemispherically-shaped, cervix-covering vaginal product. The vaginal product is folded upon itself and fitted, while in the folded condition, into the inserter so that an indicating means on the inserter will reveal the position of the folded vaginal product in vivo. The vaginal product is discharged from the inserter by squeezing the bulb at the end of the handle, thereby inverting a diaphragm located at the opposite end of the inserter and discharging the vaginal product from the inserter while oriented so as to cover the cervix.

5 Claims, 5 Drawing Figures

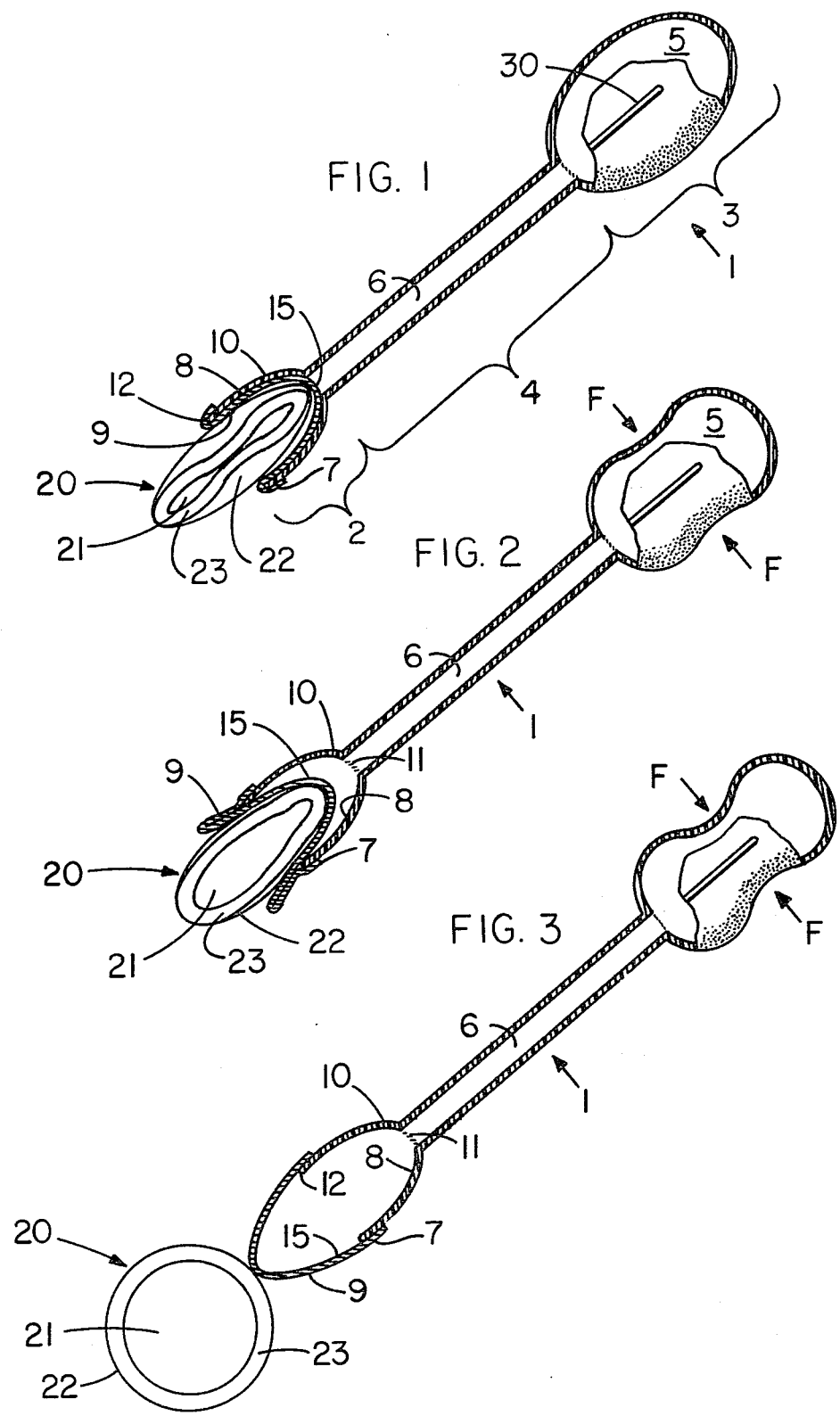

INSERTER FOR VAGINAL PRODUCT

TECHNICAL FIELD

The present invention relates to an apparatus for inserting a vaginal product such as a cervix-covering pessary.

More particularly, the present invention relates to an apparatus which ensures proper orientation of the pessary relative to the cervix so that the installed pessary will achieve its intended purpose.

BACKGROUND ART

Hemispherically-shaped pessaries designed to cover the cervix are generally known in the prior art. Such pessaries are used for various purposes, but most typically are employed as a vaginal contraceptive to prevent pregnancy. A particularly preferred cervix-covering pessary comprises a vaginal contraceptive of the type generally disclosed in U.S. Pat. No. 4,198,976 issued to Drobish et al. on Apr. 22, 1980, said patent being hereby incorporated herein by reference. The cervix-covering, vaginal contraceptive disclosed in the aforementioned patent to Drobish et al. is generally hemispherically shaped, and delivers spermicidal surfactant. The concave portion of the contraceptive unit is designed to cover the cervix in-use. Accordingly, proper installation of the unit in the vaginal cavity is of critical importance.

Pessary insertion devices of various types are also known in the prior art. U.S. Pat. No. 2,540,325 issued to De Bray et al. on Feb. 6, 1951 discloses a pessary and an inserter which may be threadedly engaged therewith. After the pessary has been inserted into position, the handle must be unthreaded from the lower end of a shaft which is secured to a cover in the pessary.

U.S. Pat. No. 2,818,856 issued to Kohl on Jan. 7, 1958 discloses a cervical cap applicator which is mechanically actuated. The cap is deformed as generally shown in FIG. 4 by advancing sleeve 26 along arms 22, 24 to permit insertion within the vaginal canal. Upon final seating of the cervical cap, the indicator rod 30 is advanced lengthwise in tubular handle 16, and the resulting outward displacement of the indicator or gauge knob 30a from the handle's end flange 16a indicates the fact of completion of the installation.

U.S. Pat. No. 2,830,582 issued to Ljung on Apr. 15, 1958 discloses yet another pessary introducer. However, the pessary is disengaged from the introducer by disengaging the lower edge of bead 18 from the recess 2 on the introducer by means of the forefinger of the user's free hand. Accordingly, the user's hand must be inserted into the vaginal cavity during the pessary insertion process.

French Pat. No. 1,271,008 issued to Seyberlich on Jan. 12, 1962 discloses an inserter for a cervix-fitting device comprising a squeeze bulb 9 connected to a suction cup 8 by means of a passageway 10. As shown in FIG. 5, the suction cup is caused to adhere to the surface 1 of the member to be inserted into the cervix opening by means of vacuum created by momentary deformation of bulb 9. Since the volume of the squeeze bulb 9 is large in relation to the size of the suction cup 8, it would appear that further squeezing of the bulb after insertion of the cervix-fitting device vitiates the vacuum, thereby discharging the device inserted into the cervix opening from the suction cup 8.

Such prior art vaginal product insertion devices are, however, deficient in one or more respects. Namely, they are difficult for the operator to use without significant training, they are complex to manufacture, they are high in cost due to the presence of numerous moving parts, and, at least in some instances, they require insertion of the user's hand into the body cavity to discharge the pessary from the inserter. Furthermore, the degree of control which the operator can exert over the pessary is quite limited after insertion of the unit into the body cavity, thereby making reliable placement over the cervix difficult for the untrained operator.

Accordingly, it is an object of the present invention to provide an apparatus for safely and reliably installing a generally hemispherically shaped pessary over the cervix, which apparatus minimizes the chance of injury to the operator or damage to the pessary during the insertion process.

It is another object of the present invention to provide such an insertion apparatus which permits the operator to control both the speed of ejection and the pressure applied to the pessary during the discharge process.

Another object of the present invention is to provide improved gripping of the pessary during insertion to minimize the chance of prematurely discharging the unit into the vaginal canal prior to alignment with the cervix.

Another object of the present invention is to ensure that the concave surface of the pessary covers the cervix by providing suitable orientation indicia on that portion of the insertion apparatus which is external to the user's body during the insertion process.

Another object of the present invention to provide a pessary inserter wherein the operator, whether the wearer or a third party administering treatment to the wearer, need only touch the handle of the inserter to complete the insertion process once the pessary has been installed thereon.

It is still a further object of the present invention to provide an insertion apparatus which can be easily manufactured at low cost, thereby facilitating either partial or complete disposal after a single use.

DISCLOSURE OF THE INVENTION

In a preferred embodiment, an apparatus for safely and reliably inserting a resilient, substantially hemispherically shaped, cervix-covering pessary into the human body without soiling of the operator's hands is provided. The apparatus preferably comprises a substantially rigid bowl having a size and shape at least partially conforming to the pessary when the pessary is folded upon itself to facilitate insertion into the vaginal canal. A resiliently deformable diaphragm substantially conforming to the bowl is disposed within the bowl and secured in sealed relation to the bowl about its periphery. A substantially rigid neck portion is secured to the exterior of the bowl, said neck portion being oriented substantially perpendicular to the bottom of said bowl and having a length sufficient to apply said pessary to the cervix when the neck portion of the apparatus is inserted into the vaginal canal. A resiliently deformable handle portion is secured to the substantially rigid neck portion, said resiliently deformable handle portion comprising a resiliently deformable, fluid-containing chamber in fluid communication with the area intermediate the rigid bowl and the unsecured portion of the resiliently deformable diaphragm through said neck portion.

The chamber contains a volume of fluid sufficient to substantially invert the unsecured portion of the diaphragm from the bowl when the resiliently deformable handle is squeezed, thereby discharging the folded pessary from the bowl in a predetermined orientation. In a particularly preferred embodiment, means are provided on the handle of said apparatus to indicate the orientation of the pessary in the bowl after insertion of the bowl and the neck portion of the apparatus into the vaginal canal. The indicating means on the handle allow the operator to properly orient the pessary relative to the cervix prior to discharging the pessary from the bowl.

BRIEF DESCRIPTION OF THE DRAWINGS

While the specification concludes with claims particularly pointing out and distinctly claiming the subject matter which is regarded as the present invention, it is believed that the invention will be better understood from the following description taken in connection with the accompanying drawings in which:

FIG. 1 is a simplified, partially segmented and partially cross-sectioned illustration of a preferred insertion apparatus of the present invention shown after a hemispherically shaped, cervix-covering pessary has been inserted into the bowl of the apparatus;

FIG. 2 is a view generally similar to FIG. 1, showing the pessary as it is being discharged from the bowl by the application of force to the handle;

FIG. 3 is a view generally similar to FIGS. 1 and 2, showing the condition of both the inserter and the pessary after the pessary has been fully discharged from the bowl by application of force to the handle;

DETAILED DESCRIPTION OF THE INVENTION

Figure 4:
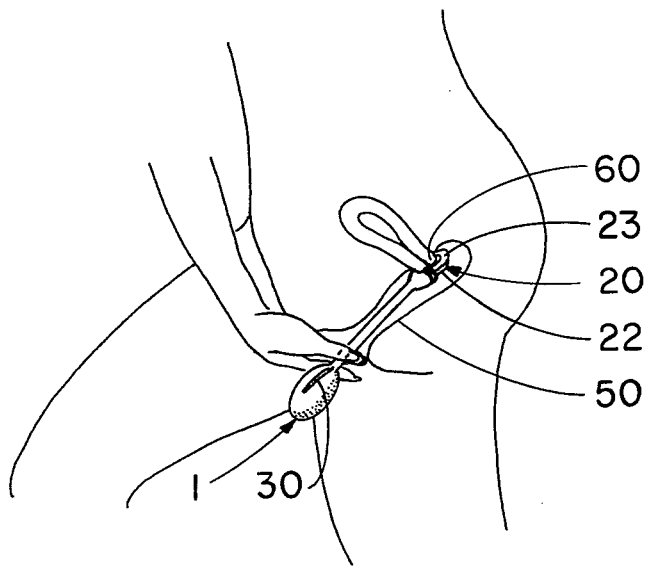
FIG. 4 is a simplified illustration showing an insertion apparatus containing a cervix-covering pessary, as generally illustrated in FIG. 1, after insertion thereof into the vaginal canal, but prior to discharge of the pessary from the insertion apparatus.

Referring to FIG. 1, there is shown a preferred insertion apparatus 1 of the present invention. While the present invention is by no means limited to the embodiment illustrated in FIG. 1, the invention will, for simplicity, be described in connection with the illustrated embodiment. In a particularly preferred embodiment, the insertion apparatus 1 of the present invention is constructed in a manner generally similar to the apparatus disclosed in U.S. Pat. No. 4,191,517 entitled METHOD AND APPARATUS FOR IMPARTING A PREDETERMINED SHAPE TO PRODUCT OF DOUGH-LIKE CONSISTENCY and issued to Byrd et al. on Mar. 4, 1980, said patent being hereby incorporated herein by reference. The illustrated insertion apparatus 1 preferably comprises a substantially rigid bowl portion 2 joined at a point along its exterior surface 10 to a neck portion 4 which, in a preferred embodiment is also substantially rigid, said neck portion in turn being joined to a resiliently deformable handle portion 3. If desired, the bowl portion, neck portion and handle portion may all be cylindrical in cross-section. Disposed within the bowl portion 2 of the insertion apparatus 1 is a resiliently deformable diaphragm 7 secured in sealed relation to the outermost surface of the bowl portion about its entire periphery by any of several means well known in the art, i.e., heat sealing, adhesive, etc. Alternatively, the diaphragm 7 may be releasably secured about its periphery to the outermost surface of the bowl portion 2 by any of several means well known in the art, i.e., an O-ring which grips the periphery of said diaphragm and resides within a circumferential groove formed in the exterior surface of the bowl portion. In the illustrated embodiment, the bowl portion 2 is substantially elliptical along its length, and is preferably so sized that it will engage approximately one-half of the cervix-covering pessary 20 when the pessary is folded about itself and inserted as generally shown in FIG. 1.

In the illustrated embodiment, the handle portion 3 of the insertion apparatus forms a totally enclosed, resiliently deformable chamber 5 which, by virtue of passageway 6 and orifice 11, remains in fluid communication with the area intermediate the interior surface 8 of bowl portion 2 and the interior surface 15 of resiliently deformable diaphragm 7.

In the illustrated embodiment, the substantially rigid bowl portion 2 and the substantially rigid neck portion 4 permit the use of a resiliently deformable handle portion 3 without adversely affecting the mechanical strength of the insertion apparatus 1.

As is generally shown in FIG. 1, a cervix-covering pessary 20 of the type generally disclosed in U.S. Pat. No. 4,198,976 issued to Drobish et al. on Apr. 22, 1980 is folded upon itself such that its concave cervix-contacting surface 21 is nearly brought in contact with itself adjacent hemispherical rim 23, thereby exposing the non-cervix-contacting convex outermost surface 22 of the pessary 20 to the outermost surface 9 of diaphragm 7. The large contact area between the outermost surface 22 of the pessary and the outermost surface 9 of the diaphragm permits the diaphragm to firmly grasp the pessary and exert a high level of control thereover throughout the insertion process.

FIG. 2 illustrates the manner in which insertion apparatus 1 functions to discharge the pessary 20 from the bowl 2 without need for any direct contact with the pessary by the operator. In particular, a pair of opposing forces, designated F in FIG. 2, are applied by squeezing the resiliently deformable handle portion 3 of the insertion apparatus 1, thereby deforming the handle portion. Because the diaphragm 7 is secured in sealed relation to the bowl portion 2 of the dispensing apparatus, the volume of fluid contained within the resiliently deformable chamber 5 of handle portion 3 is not allowed to escape from the interior portions of the insertion apparatus. Accordingly, the fluid from chamber 5, which preferably comprises a compressible fluid such as air, is displaced through passageway 6 and orifice 11 so as to exert force against the unsecured portion of the interior surface 15 of the resiliently deformable diaphragm 7. This causes the unsecured portion of the diaphragm 7 to separate from the interior surface 8 of the bowl portion 2 of the insertion apparatus. As greater and greater forces F are applied to the resiliently deformable handle portion 3 of the dispensing apparatus, the diaphragm 7 is gradually inverted from the substantially rigid bowl portion 2 of the dispensing apparatus. Because the diaphragm unrolls as generally shown in FIG. 2, the pessary 20 is maintained under positive control in the inserter almost throughout the entire discharge cycle. This ensures that the concave surface 21 of the pessary 20 remains in alignment with an indicating means 30 provided on handle portion 3 of the insertion apparatus 1. In the illustrated embodiment, the indicating means comprises a raised rib 30, said raised rib enabling the operator to determine the orientation of the pessary 20 either by tactile impression or visually. Thus, for the operator to be assured that the pessary 20 will be discharged in the desired orientation it is only necessary that the operator note the position of the installed pessary relative to the visual or tactile indicator 30 on the handle portion 3.

Referring to FIG. 2, as the pessary is discharged from the insertion apparatus 1, it partially reassumes its unrestrained hemispherical shape. When, as shown in FIG. 3, the diaphragm 7 is completely inverted, the pessary 20 is completely discharged from the insertion apparatus 1 and is allowed to completely reassume its unrestrained hemispherical shape.

An insertion apparatus 1 of the present invention minimizes the chance of damage to the pessary 20, since there are no sharp mechanical members which come in contact with the pessary during insertion of the pessary into the bowl, insertion of the apparatus into the vaginal canal, or discharge of the pessary from the bowl. Since both the speed and pressure of discharge applied to the pessary 20 by the diaphragm 7 are directly dependent upon the application of forces F to the resiliently deformable handle portion 3, the operator is in complete control of both factors throughout the placement process. In addition, there is substantially no slippage of the pessary 20 relative to the outermost surface 9 of the diaphragm once the pessary has been inserted into the bowl portion 2. Accordingly, there is minimal chance of prematurely discharging the pessary. Furthermore, there is very little chance of misorienting the pessary relative to the cervix, particularly if the operator observes the position of indicating means 30 on the handle portion 3.

Figure 5:
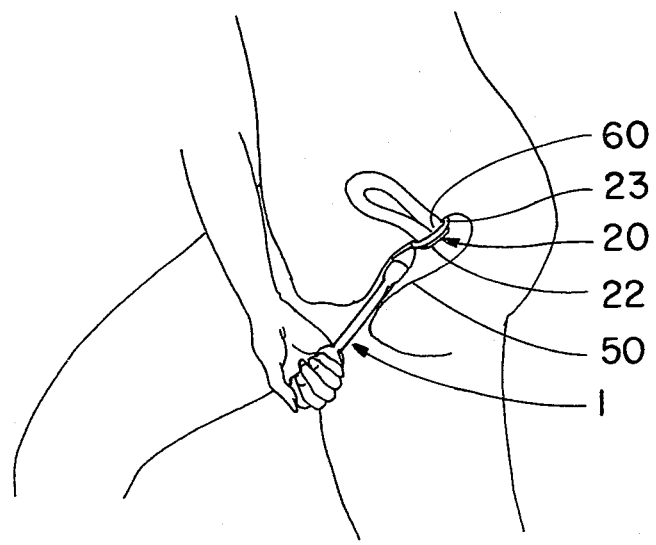
FIG. 5 is a view generally similar to that of FIG. 4, but showing the condition of the pessary after discharge from the insertion apparatus and placement over the cervix.

The pessary insertion process is illustrated in simplified form in FIG. 4, wherein the applicator 1 has been inserted into the vaginal canal 50 so that the center of the pessary 20 is in approximate alignment with the opening 60 of the cervix. In the illustrated embodiment, the pessary 20 has been inserted into the applicator 1 such that its concave surface 21 is substantially aligned with indicator 30, as generally shown in FIG. 1. To place the pessary in service, the operator need only squeeze the handle portion of the applicator 1, as generally shown in FIG. 5. This results in discharge of the pessary 20 from the applicator such that its rim 23 surrounds the cervix, while its convex outermost surface 22 is oriented adjacent the bottom of the vaginal canal 50.

As has been pointed out earlier herein, diaphragm 7 may, if desired, be permanently secured about its periphery in sealed relation to the bowl portion 2 of the insertion apparatus 1 by any of a number of suitable means known in the art. If, however, it is desired to dispose of only the diaphragm 7 after each use or if it is desired to provide a pneumatically actuated insertion apparatus capable of normal functioning at any atmospheric pressure, releasable diaphragm securement means well known in the art may be provided. As will be appreciated by those skilled in the art, temporarily removing the diaphragm equalizes the pressure inside and outside the insertion apparatus. In the event a releasable diaphragm is provided, it is, of course, preferable that the particular releasable securement means employed present a smooth surface along the exterior of the rigid bowl portion 2 of the insertion apparatus 1 to avoid the chance of discomfort or injury during insertion into the vaginal canal.

As will further be appreciated by those skilled in the art, the particular material used to form the resiliently deformable diaphragm 7 is normally chosen for strength, conformability, and hygienic properties. In a particularly preferred embodiment of the present invention an elastomeric film of ethyl vinyl acetate, such as ULTATHENE UE632 available from U.S. Industrial Chemical Corporation of New York, N.Y., having an initial thickness of approximately 1.2 mils may be vacuum thermoformed to fit the cavity within bowl portion 2 of the insertion apparatus 1. However, any elastomeric film having suitable strength, conformability, release and hygienic properties could be employed with equal facility. As will be appreciated by those skilled in the art, diaphragm 7 could also be injection molded by means well known in the art or formed from a hygienically acceptable natural or synthetic latex. One particularly preferred material is a natural latex identified as HARTEX 101 available from Firestone Synthetic Rubber & Latex Company of Akron, Ohio.

The bowl, neck and handle portions of an insertion apparatus of the present invention may readily be blow molded from hygienically acceptable synthetic plastic materials, such as Type 5602A blow molding grade polyethylene available from Chemplex Corporation of Rolling Meadows, Ill. Blow molding techniques well known in the art may be utilized to profile the thickness of the various portions so as to provide a substantially rigid bowl portion 2, a substantially rigid neck portion 4 and a resiliently deformable handle portion 3. If desired, the components could be separately formed or fabricated and thereafter assembled, either permanently or temporarily.

The particular means utilized to secure the periphery of the diaphragm 7 to the bowl portion 2 of the insertion apparatus 1 will, of course, depend upon their compatibility with one another. Compatible materials may be heat sealed to one another by means well known in the art, while incompatible materials may require the use of adhesives, mechanical securement means, or the like.

The chief design criteria to be considered in sizing the resiliently deformable chamber 5 of the handle portion 3 in relation to the size of the bowl portion 2 is that the volume of fluid, i.e., gas, air, liquid, etc., displaced from the chamber 5 must be sufficient to completely expand and invert the diaphragm 7 from the bowl portion, substantially as shown in FIG. 3, to facilitate discharge of the pessary 20 without manual intervention.

An overall length of $3\frac{1}{2}$ to 4 inches for neck portion 4 has been found effective for inserting a vaginal contraceptive of the type generally disclosed in the aforementioned patent to Drobish et al.

As will be appreciated by those skilled in the art, insertion apparatus of the present invention are not only easy to manufacture at relatively low cost, but in addition provide improved sanitation since the operator's hands need not touch the interior portions of the vaginal canal during the insertion process.

It is to be understood that the form of the invention herein illustrated and described is to be taken as a preferred embodiment. Various changes or omissions may be made without departing from the spirit or scope of the invention as described in the appended claims.

Having thus defined and described the invention, what is claimed is:

1. An apparatus for safely and reliably inserting a resilient, substantially hemispherically-shaped, cervix-covering pessary into the human body without soiling of the operator's hands, said apparatus comprising:
   (a) a substantially rigid bowl having a size and shape at least partially conforming to said pessary when said pessary is folded upon itself to facilitate insertion into the vaginal canal;
   (b) a resiliently deformable diaphragm substantially conforming to and disposed within said bowl secured in sealed relation thereto about its periphery;
   (c) a substantially rigid neck portion secured to the exterior of said bowl, said neck portion being oriented substantially perpendicular to the bottom of said bowl and having a length sufficient to apply said pessary to said cervix when said neck portion is inserted into the vaginal canal;
   (d) a resiliently deformable handle portion secured to said substantially rigid neck portion, said resiliently deformable handle portion comprising a resiliently deformable fluid-containing chamber in fluid communication with the area intermediate said rigid bowl and the unsecured portion of said resiliently deformable diaphragm through said neck portion, said chamber containing a volume of fluid sufficient to substantially invert the unsecured portion of said diaphragm from said bowl when said resiliently deformable handle is squeezed, thereby discharging said folded pessary from said bowl in a predetermined orientation; and
   (e) means on said handle to indicate the orientation of said pessary in said bowl after insertion of said bowl and said neck portion into the vaginal canal to allow the operator to properly orient said pessary relative to the cervix prior to discharging said pessary from said bowl.

2. The apparatus of claim 1, wherein said resiliently deformable diaphragm is releasably secured in sealed relation to said bowl.

3. The apparatus of claim 1, wherein said resiliently deformable diaphragm is comprised of elastomeric film.

4. The apparatus of claim 1, wherein said substantially rigid bowl, said substantially rigid neck portion and said resiliently deformable handle portion are integrally formed of synthetic plastic.

5. The apparatus of claim 1, wherein said means on said handle to indicate the orientation of said pessary in said bowl comprises a raised rib.

* * * * *